US009168046B2

(12) United States Patent
Weisshaupt et al.

(10) Patent No.: US 9,168,046 B2
(45) Date of Patent: Oct. 27, 2015

(54) SURGICAL SLIDING SHAFT INSTRUMENT AND SLIDING SHAFT

(75) Inventors: Dieter Weisshaupt, Immendingen (DE); Konstantin Faulhaber, Frittlingen (DE); Peter Schulz, Loeffingen (DE); Markus Nesper, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 110 days.

(21) Appl. No.: 13/196,219

(22) Filed: Aug. 2, 2011

(65) Prior Publication Data

US 2012/0016402 A1 Jan. 19, 2012

Related U.S. Application Data

(63) Continuation of application No. PCT/EP2010/051058, filed on Jan. 29, 2010.

(30) Foreign Application Priority Data

Feb. 6, 2009 (DE) .......................... 10 2009 008 719

(51) Int. Cl.
*A61B 17/32* (2006.01)
*A61B 17/16* (2006.01)
(Continued)

(52) U.S. Cl.
CPC ..... *A61B 17/1611* (2013.01); *A61B 2017/0046* (2013.01); *A61B 2019/4868* (2013.01)

(58) Field of Classification Search
CPC ........... A61B 17/1611; A61B 17/1604; A61B 17/3468; A61B 17/32053; A61B 2017/0046; A61B 2019/4868
USPC .................................. 606/174, 184, 206, 207
See application file for complete search history.

(56) References Cited

U.S. PATENT DOCUMENTS

| 3,902,498 A | 9/1975 | Niederer |
|---|---|---|
| 4,243,047 A | 1/1981 | Olsen |

(Continued)

FOREIGN PATENT DOCUMENTS

| DE | 33 43 867 | 6/1985 |
|---|---|---|
| DE | 295 06 466 | 8/1995 |

(Continued)

OTHER PUBLICATIONS

European Search Report for EP 10 15 2052 dated Jun. 30, 2014, 2 pages.

*Primary Examiner* — Thomas McEvoy
*Assistant Examiner* — Julie A Szpira
(74) *Attorney, Agent, or Firm* — Lipsitz & McAllister, LLC

(57) ABSTRACT

In order to improve a sliding shaft for a surgical sliding shaft instrument, wherein the sliding shaft defines a longitudinal direction and comprises a first shaft part and a second shaft part which are arranged such that they are displaceable relative to each other, wherein said first shaft part carries a first tool element and said second shaft part carries a second tool element, wherein the second shaft part has a cut material collector with an inlet opening which is bounded by the second tool part and extends therefrom in the proximal direction, such that the cut material collector can be emptied in a simple and rapid manner, it is proposed that the cut material collector should have at least one emptying opening which is formed on the proximal side of the inlet opening and that the at least one emptying opening should be open in a lateral emptying direction which is oriented perpendicularly or substantially perpendicularly with respect to the longitudinal direction and parallel or substantially parallel to a contact plane defined by a lower surface of the second shaft part.

25 Claims, 8 Drawing Sheets

Figure 1:
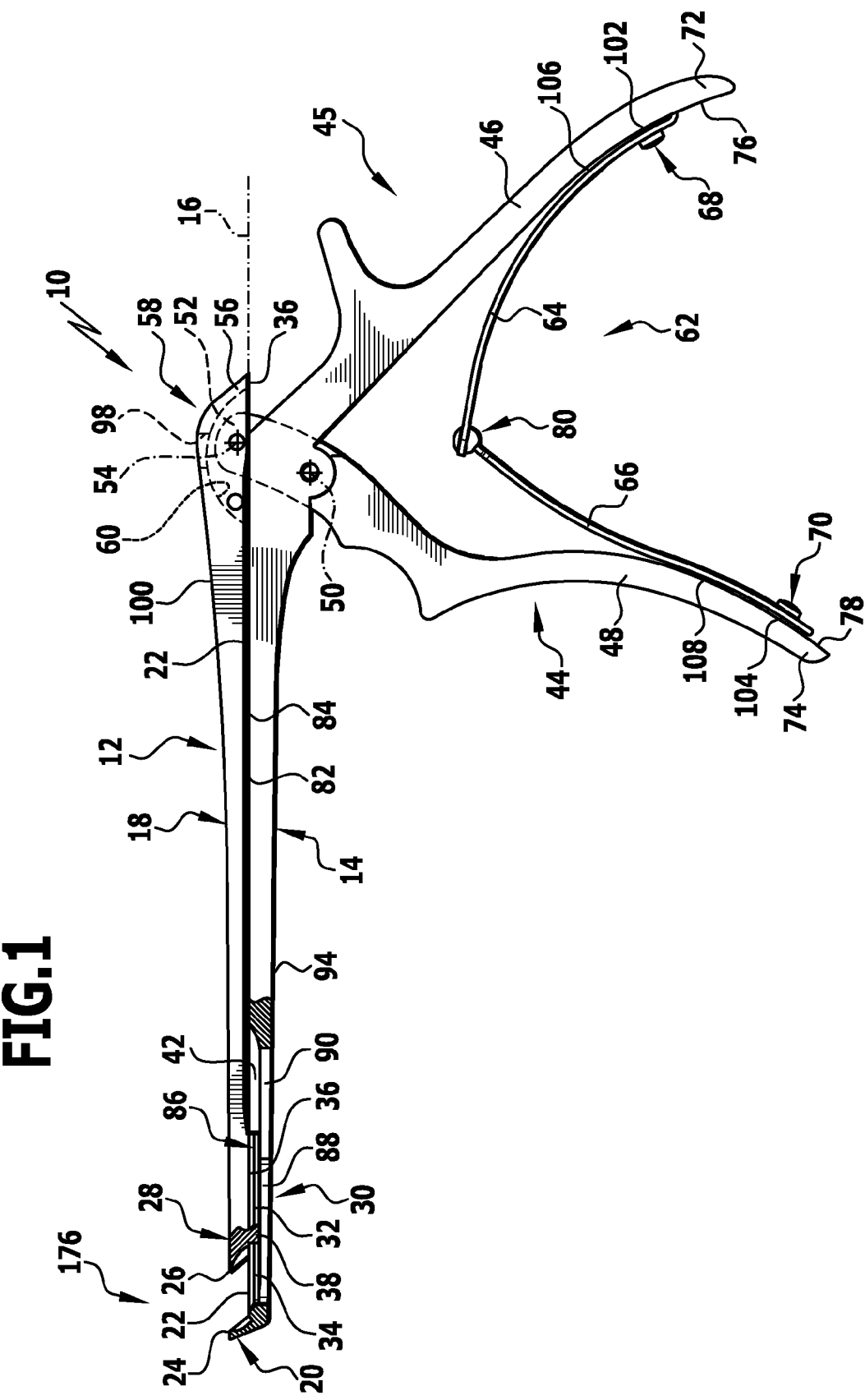

(51) Int. Cl.
*A61B 17/00* (2006.01)
*A61B 19/00* (2006.01)

(56) References Cited

U.S. PATENT DOCUMENTS

| | | | |
|---|---|---|---|
| 5,385,570 A * | 1/1995 | Chin et al. | 606/170 |
| 5,813,380 A | 9/1998 | Takahashi et al. | |
| 6,200,320 B1 | 3/2001 | Michelson | |
| 6,261,294 B1 | 7/2001 | Stihl et al. | |
| 6,520,979 B1 * | 2/2003 | Loubens et al. | 606/205 |
| 6,638,280 B2 | 10/2003 | Agbodoe | |
| 6,695,849 B2 | 2/2004 | Michelson | |
| 7,011,663 B2 | 3/2006 | Michelson | |
| 7,297,147 B2 | 11/2007 | Michelson | |
| 7,621,932 B2 | 11/2009 | Wenzler | |
| 2001/0005786 A1 | 6/2001 | Michelson | |
| 2003/0069584 A1 | 4/2003 | Agbodoe | |
| 2004/0044346 A1 | 3/2004 | Boury | |
| 2004/0186499 A1 * | 9/2004 | Michelson | 606/170 |
| 2005/0090829 A1 | 4/2005 | Martz et al. | |
| 2006/0085021 A1 | 4/2006 | Wenzler | |
| 2006/0149271 A1 | 7/2006 | Michelson | |
| 2007/0039403 A1 | 2/2007 | Manwaring et al. | |
| 2007/0093843 A1 | 4/2007 | Schneiter | |
| 2008/0092884 A1 | 4/2008 | Hansen et al. | |
| 2008/0221606 A1 | 9/2008 | Faulhaber et al. | |

FOREIGN PATENT DOCUMENTS

| | | |
|---|---|---|
| DE | 103 20 477 | 7/2004 |
| DE | 20 2004 015 643 | 12/2004 |
| DE | 20 2004 015 990 | 12/2004 |
| DE | 20 2007 003 519 | 7/2007 |
| DE | 602 23 978 | 12/2008 |
| EP | 1 967 145 | 9/2008 |
| WO | 95/05123 | 2/1995 |
| WO | 99/37221 | 7/1999 |

* cited by examiner

SURGICAL SLIDING SHAFT INSTRUMENT AND SLIDING SHAFT

This application is a continuation of international application number PCT/EP2010/051058 filed on Jan. 29, 2010 and claims the benefit of German application number 10 2009 008 719.2 filed on Feb. 6, 2009.

The present disclosure relates to the subject matter disclosed in international application number PCT/EP2010/051058 of Jan. 29, 2010 and German application number 10 2009 008 719.2 of Feb. 6, 2009, which are incorporated herein by reference in their entirety and for all purposes.

FIELD OF THE INVENTION

The present invention relates to sliding shafts for a surgical sliding shaft instrument generally, and more specifically to a sliding shaft for a surgical sliding shaft instrument which said sliding shaft comprises a first shaft part and a second shaft part that are arranged such as to be moveable relative to one another and also a guidance device for guiding a movement of the second shaft part relative to the first shaft part, which said first shaft part carries a first tool element and which said second shaft part carries a second tool element, which said first and second tool elements cooperate with and/or abut each other in a working position and are spaced from each other in a position that is deflected from the working position or are spaced further from each other than in the working position, wherein the guidance device comprises at least one first guide element which is arranged on the first shaft part and at least one second guide element which is arranged on the second shaft part and cooperates with the at least one first guide element, wherein said guide elements interlock in shape-fitting manner for guiding a movement of the second shaft part relative to the first shaft part.

Furthermore, the present invention relates to surgical sliding shaft instruments generally, and more specifically to a surgical sliding shaft instrument comprising an instrument handle and a sliding shaft which is operable by means of the instrument handle, said sliding shaft comprising a first shaft part and a second shaft part which are arranged such as to be moveable relative to each other and also a guidance device for guiding a movement of the second shaft part relative to the first shaft part, which said first shaft part carries a first tool element and which said second shaft part carries a second tool element, wherein said first and second tool elements cooperate with and/or abut each other in a working position and are spaced from each other in a position that is deflected from the working position or are spaced further from each other than they are in the working position, wherein the guidance device comprises at least one first guide element which is arranged on the first shaft part and at least one second guide element which is arranged on the second shaft part and cooperates with the at least one first guide element wherein said first and second guide elements interlock in shape-fitting manner for guiding a movement of the second shaft part relative to the first shaft part.

BACKGROUND OF THE INVENTION

Surgical sliding shaft instruments of the type described hereinabove in the form of bone punches for example are known. They are constructed in such a manner that the two shaft parts forming the sliding shaft are guided directly upon one another. For this purpose, there are provided so-called internal guide elements which form the guidance device and which are arranged or formed on the surfaces of the shaft parts that rest upon one another. The two shaft parts, which are also referred to as an upper slide part and a lower slide part, abut each other directly. This, however, has the disadvantage that when cleaning or even when using the instrument, fluid can be sucked in between the shaft parts that abut each other. It is practically impossible to remove this fluid without dismantling the instrument.

SUMMARY OF THE INVENTION

In with a first aspect of the invention, a sliding shaft for a surgical sliding shaft instrument is provided which defines a longitudinal direction and comprises a first shaft part and a second shaft part which are arranged such as to be displaceable relative to each other. Said first shaft part carries a first tool element and said second shaft part carries a second tool element. The second shaft part comprises a cut material collector having an inlet opening which is bounded by the second tool part and extends therefrom in the proximal direction. The cut material collector comprises at least one emptying opening which is formed on the proximal side of the inlet opening. The at least one emptying opening is open in a lateral emptying direction, which emptying direction is oriented perpendicularly or substantially perpendicularly to the longitudinal direction and parallel or substantially parallel to a contact plane defined by a lower surface of the second shaft part.

In a second aspect of the invention, a surgical sliding shaft instrument comprises an instrument handle and a sliding shaft that is operable by means of the instrument handle. Said sliding shaft defines a longitudinal direction and comprises a first shaft part and a second shaft part which are arranged such that they are displaceable relative to each other. Said first shaft part carries a first tool element and said second shaft part carries a second tool element. The second shaft part has a cut material collector having an inlet opening which is bounded by the second tool element and extends therefrom in the proximal direction. The cut material collector has at least one emptying opening which is formed at the proximal side of the inlet opening. The emptying opening is open in a lateral emptying direction, which said emptying direction is oriented perpendicularly or substantially perpendicularly to the longitudinal direction and parallel or substantially parallel to a contact plane defined by a lower surface of the second shaft part.

In a third aspect of the invention, a sliding shaft for a surgical sliding shaft instrument is provided which defines a longitudinal direction and comprises a first shaft part and a second shaft part which are arranged such as to be displaceable relative to each other. Said first shaft part carries a first tool element and said second shaft part carries a second tool element. The second shaft part comprises a cut material collector having an inlet opening which is bounded by the second tool part and extends therefrom in the proximal direction. The second shaft part is formed in at least two parts, and comprises a tool part which comprises the second tool element and a sliding part which is connected to the tool part

BRIEF DESCRIPTION OF THE DRAWING FIGURES

Figure 2:
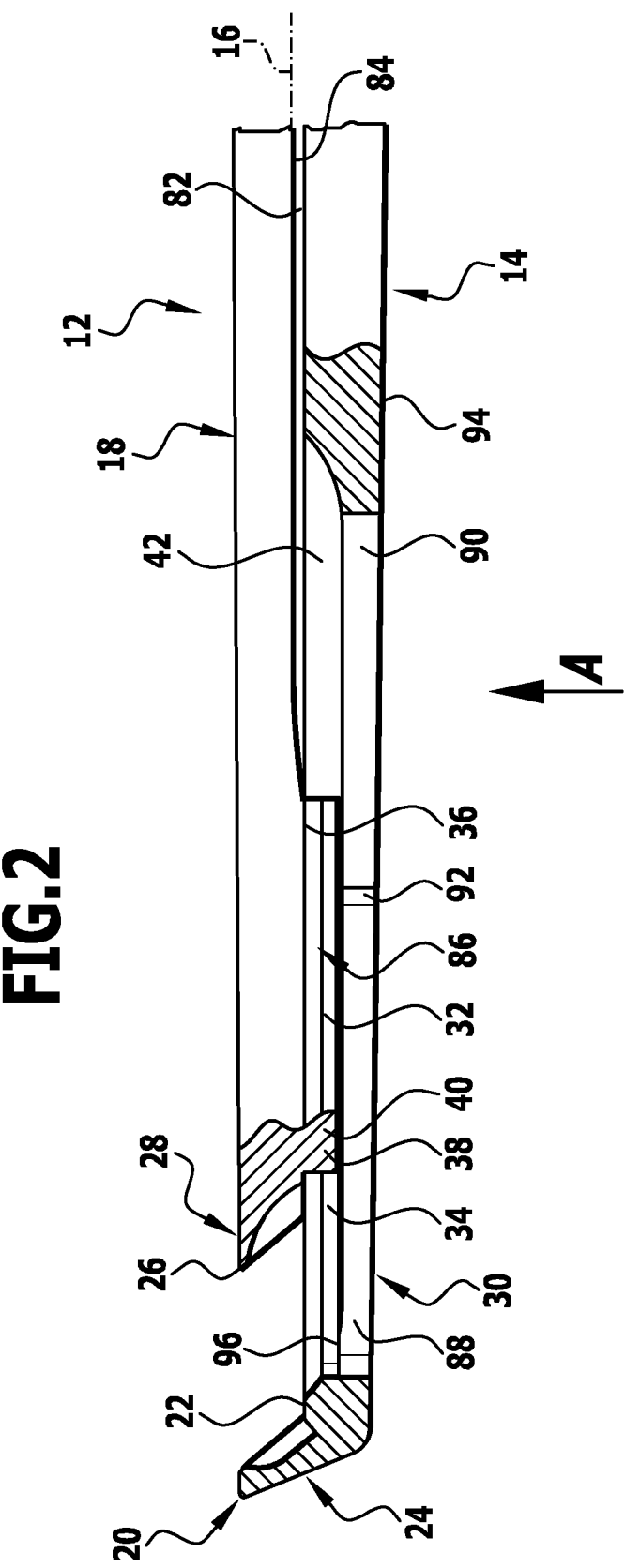
Figure 3:
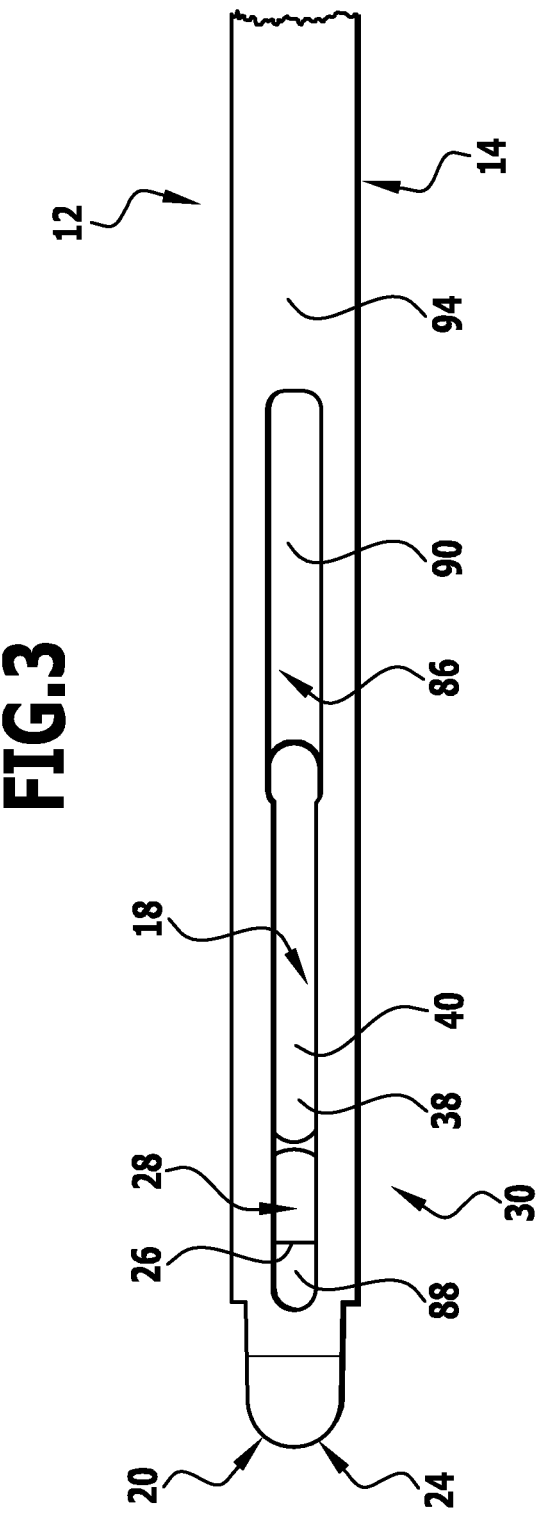
Figure 4:
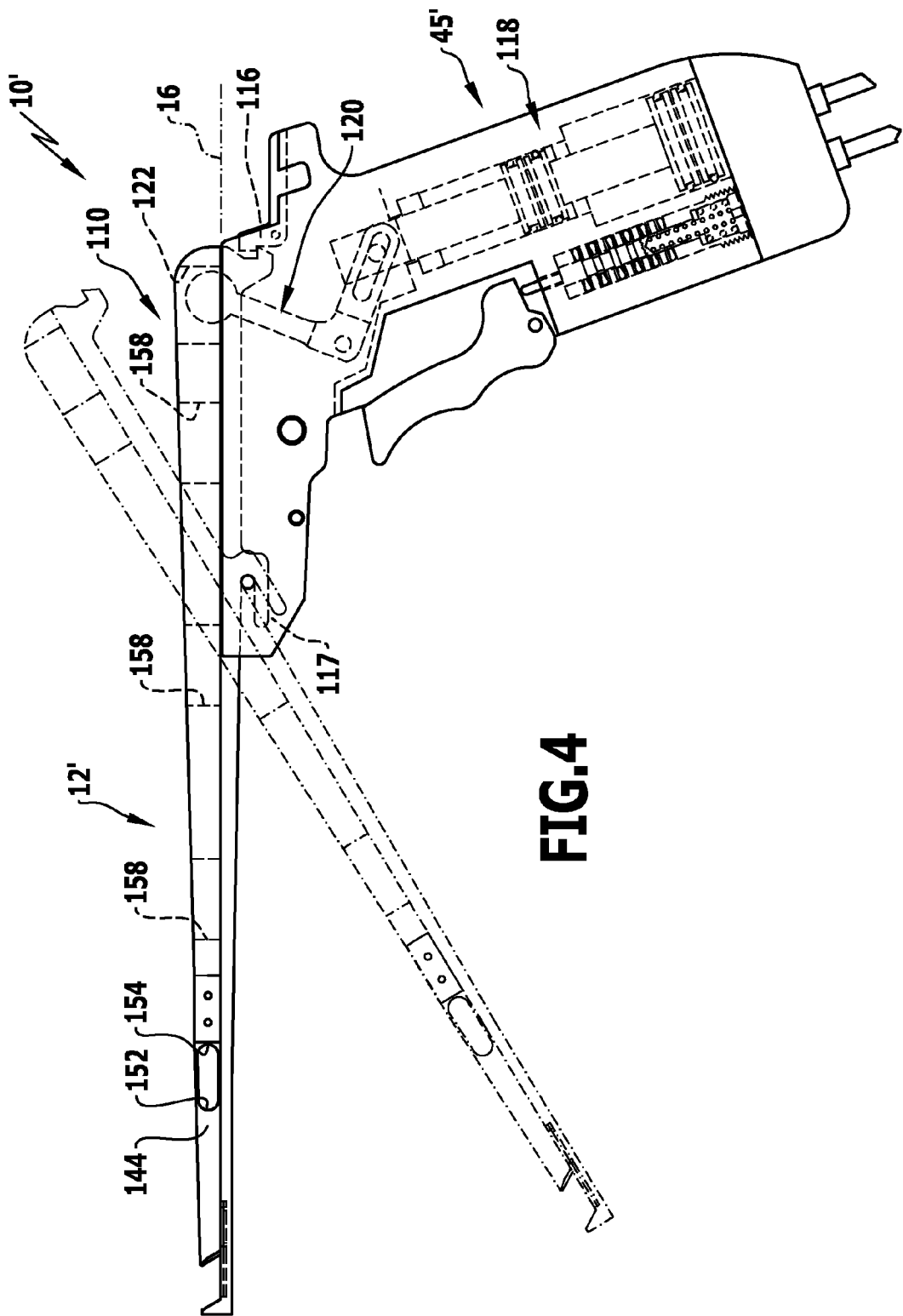
Figure 5:
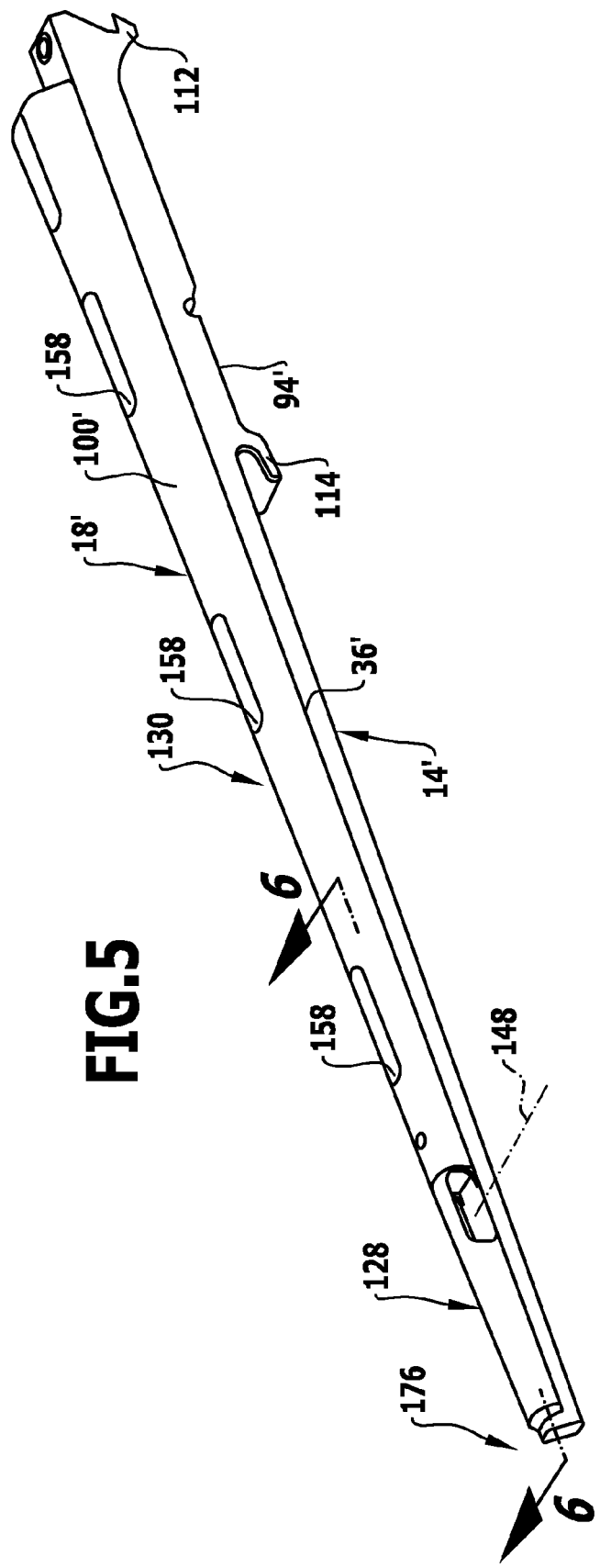
Figure 6:
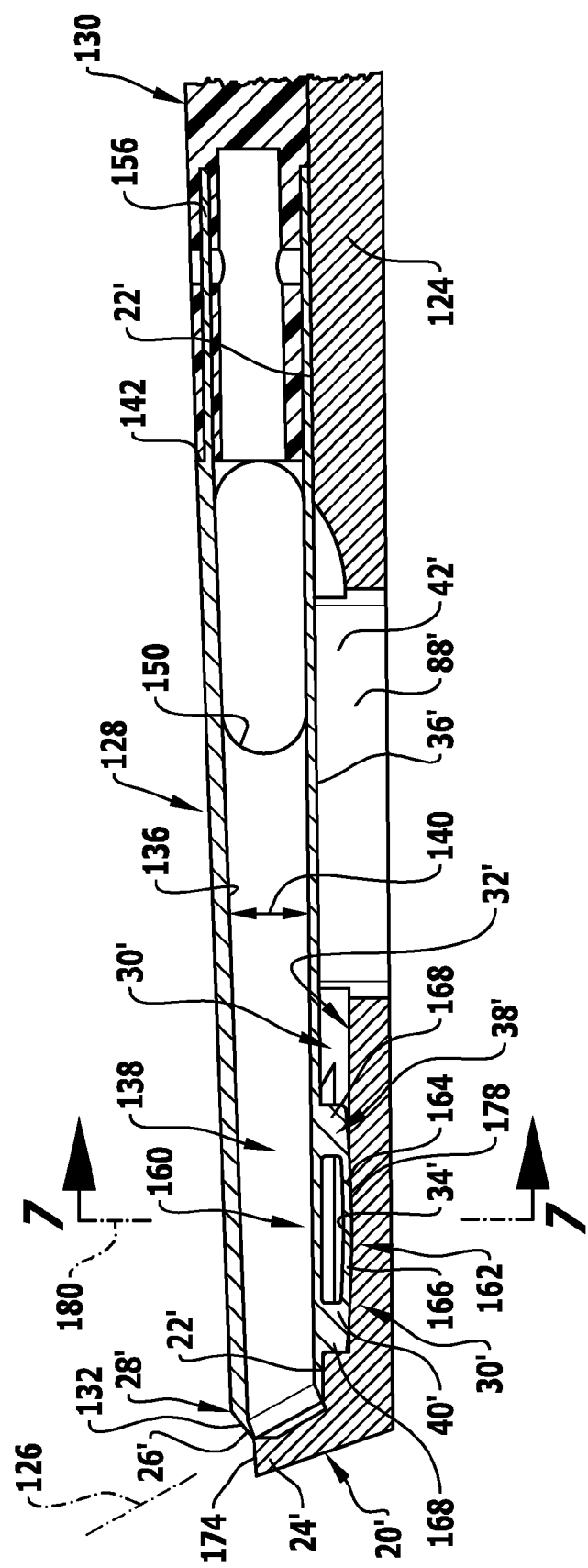
Figure 7:
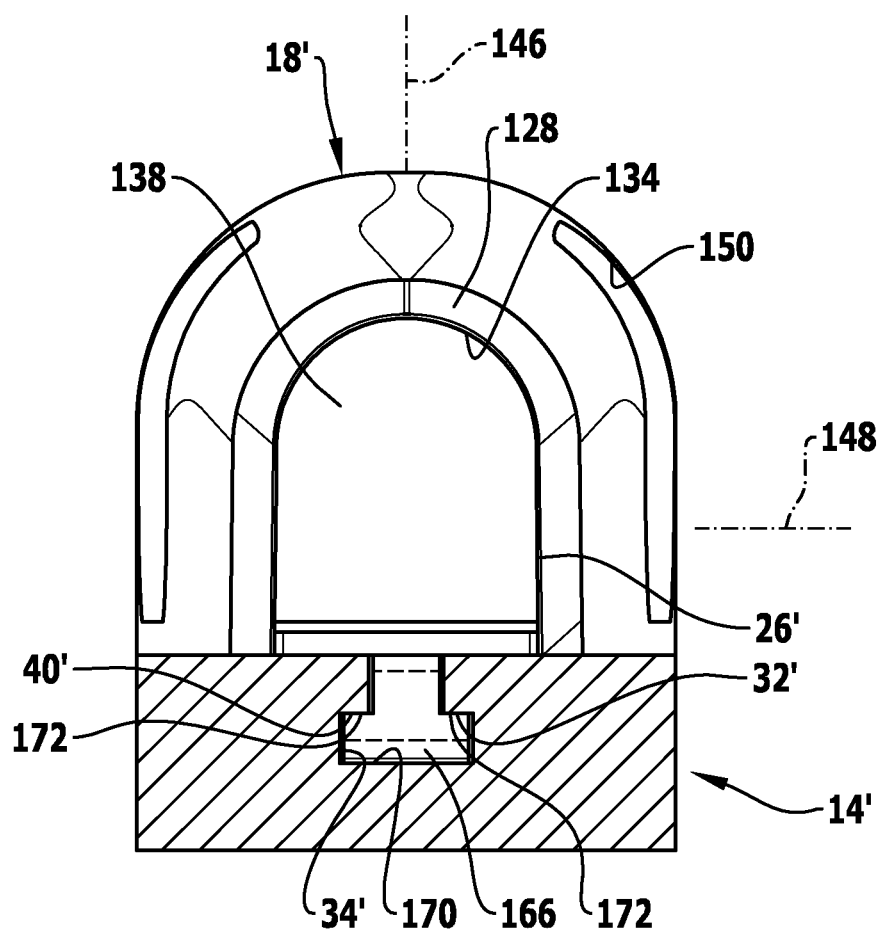

The foregoing summary and the following description may be better understood in conjunction with the drawing figures, of which:

FIG. 1: shows a partially sectional or cut-away side view of a surgical sliding shaft instrument in the form of a bone punch;

FIG. 2: an enlarged partial view of a distal end region of the bone punch depicted in FIG. 1;

FIG. 3: a view in the direction of the arrow A in FIG. 2;

FIG. 4: a partially cut-away side view of a further exemplary embodiment of a surgical sliding shaft instrument comprising a sliding shaft and an instrument handle which is connectable thereto in releasable manner;

FIG. 5: a perspective view of the sliding shaft depicted in FIG. 4;

FIG. 6: a sectional view of the longitudinal line 6-6 in FIG. 5;

FIG. 7: a partial sectional view along line 7-7 in FIG. 6; and

Figure 8:
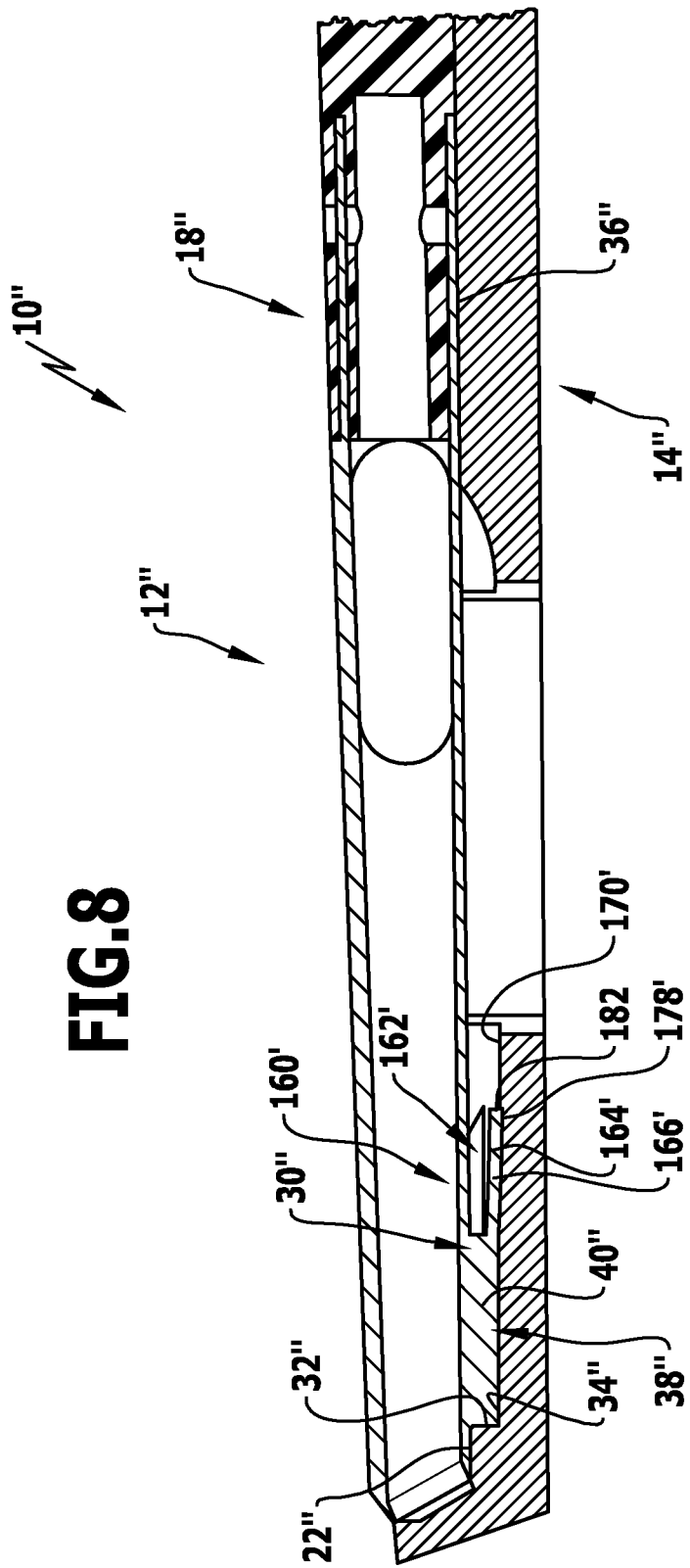

FIG. 8: a sectional view analogous to FIG. 6 of a further exemplary embodiment of a sliding shaft.

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a sliding shaft for a surgical sliding shaft instrument which defines a longitudinal direction and comprises a first shaft part and a second shaft part which are arranged such as to be displaceable relative to each other, wherein said first shaft part carries a first tool element and said second shaft part carries a second tool element, wherein the second shaft part comprises a cut material collector having an inlet opening which is bounded by the second tool part and extends therefrom in the proximal direction, wherein the cut material collector comprises at least one emptying opening which is formed on the proximal side of the inlet opening, and the at least one emptying opening is open in a lateral emptying direction, which emptying direction is oriented perpendicularly or substantially perpendicularly to the longitudinal direction and parallel or substantially parallel to a contact plane defined by a lower surface of the second shaft part.

The solution proposed in accordance with the invention makes it possible for the guidance device to be cleaned in a simple and reliable manner. The guidance device can be freed of impurities in a simple and reliable manner by means of a rinsing fluid due to the provision of a lateral opening for example.

It can be expedient furthermore, and especially too in the case of a sliding shaft of the type described hereinabove, if the first shaft part and the second shaft part only abut each other in a guidance region within which the first and the second guide elements interlock, and if, apart from this guidance region, they are spaced from each other by a cleaning gap. The cleaning gap envisaged in accordance with the invention has the advantage that impurities which enter the area between the two shaft parts can readily be removed by a process of rinsing or washing the instrument in a washing machine. The cleaning gap thus prevents liquids from being sucked in between the shaft parts which conventionally abut each other. Consequently, the instrument does not need to be dismantled for comprehensive cleaning and sterilization purposes. The cleaning gap is preferably large enough for it to be easily flushed out with a cleaning fluid.

Expediently, the size of the cleaning gap, and especially the width thereof, is sufficiently large as to prevent the occurrence of a capillary effect for a cleaning fluid. The width of the cleaning gap preferably lies in a range of between 0.2 mm and 2 mm. It is expedient, if the width of the gap falls within a range from 0.2 mm up to 1 mm, preferably 0.6 mm. For the purposes of forming the cleaning gap, the first and/or the second shaft part are provided with an appropriate recess or slot. The production process is particularly simple, if the recess, the depth of which preferably defines the width of the cleaning gap, is only provided on one shaft part. This is preferably realized by a recess in the second shaft part. Preferably, the recess extends from the guidance region in the proximal direction, optionally, up to the proximal end of the second shaft part.

It is advantageous, if the at least one first or second guide element is in the form of a guide groove and if the corresponding other guide element is in the form of a guidance projection which engages in the guide groove in interlocking manner. Secure and tilt-free guidance of the two shaft parts upon one another can be realized by virtue of the positively cooperating guide elements in the form of the guide groove and the guidance projection.

In order to achieve a defined movement parallel to a longitudinal axis defined by the sliding shaft in a simple manner, it is expedient if the at least one first or second guide element extends parallel to a longitudinal axis defined by the sliding shaft over a range which corresponds at least to a relative displacement path between the first and second shaft parts. Guidance of the shaft parts upon one another can thereby be ensured over the entire desired path of movement.

In order to ensure that the shaft parts are moveable relative to each other over a desired path of movement, it is advantageous if the other one of the guide elements extends parallel to a longitudinal axis defined by the sliding shaft over a range which is smaller than the guidance region. A path of movement or length of stroke of the two shaft parts relative to each other can then be predefined in a simple manner by appropriate choice of the extent of the first and second guide elements.

In order to enable an interlocking connection between the guide elements of the guidance device to be produced in a simple manner, it is expedient if the at least one first or the at least one second guide element is formed with an undercut on at least one side thereof. In addition thereby, it can also be ensured that the shaft parts cannot be separated from one another in a direction perpendicular to the longitudinal axis of the sliding shaft when the two guide elements are in engagement with each other.

Advantageously, the width of the guide groove transverse to the direction of motion defined by the guidance device decreases in the direction of the second shaft part. In particular thereby, the guide groove can be in the form of a dove tail groove. It would also be conceivable however, for the construction to take the form of a groove having a T-shaped cross section.

The structure of the sliding shaft is particularly simple, if provision is made for just one first and/or just one second guide element.

It is advantageous, if the one single first and/or second guide elements are arranged in the vicinity of the distal ends of the first and second shaft part. In particular in the case where the tool elements are arranged in the vicinity of the distal ends, this thereby enables optimal guidance thereof when they are cooperating with one another.

It is also expedient especially in the case of a sliding shaft of the type described hereinabove, for the guidance device to comprise at least one rinsing opening for establishing a fluid connection between a guidance space defined by the guidance device and the surroundings of the instrument. A cleaning or a rinsing fluid can then be introduced into the guidance space and also fed out therefrom through the rinsing opening. Two, three or even more rinsing openings could be provided in order to enable the guidance device to be cleaned in a simple and reliable manner.

The structure of the sliding shaft instrument can be simplified still more, if the guidance space is defined by an interior of the guide groove. In such a case, the guidance space is bounded in particular by the side walls of the groove and also the groove base which is opposite a slot defined by the guidance groove.

The guidance device can be produced in a particularly simple manner, if the at least one rinsing opening is in the form of a through opening in a side wall of the first shaft part which bounds the guide groove. In the case of a rectangular or dovetail-shaped guide groove for example, there is a total of three side walls available which can be equipped with one or more rinsing openings.

The production of the sliding shaft instrument is further simplified, if the through opening is in the form of a slot or an elongate hole.

In accordance with a further preferred embodiment of the invention, and especially too in the case of a sliding shaft of the type described hereinabove, provision may be made for the second shaft part to be constructed of at least two parts and for it to comprise a tool part, which comprises the second tool element, and a sliding part which is connected to the tool part. The at least two-piece construction of the second shaft part makes it possible, in particular, to produce a cut material collector having an internal cross section which increases in the proximal direction in a simple manner. Furthermore, the two-piece construction offers the option of making the second shaft part from two different materials. Since, particularly in the case of the second tool element of the second shaft part, this is an element subject to wear, production costs can be saved due to the two-piece construction since only the tool part has to be made of a material which fulfils the demands made on the second tool element, but not however, on the sliding part.

In order to be able to construct the second shaft part individually, it is advantageous if the sliding part is made of a sliding part material and if the tool part is made of a tool part material. Consequently, a material which is optimal for each type of use can be selected for the respective parts of the second shaft part.

It is expedient, if the sliding part material and the tool part material are different materials. This permits the special requirements for each of the parts to be taken into consideration when selecting the materials for the construction of the two parts.

Advantageously, the tool part material is a metal. In particular, the tool material is an instrument steel. A metal, and especially an instrument steel, is outstandingly suitable for the construction of a second tool element in the form of a cutting edge which can be sharpened by grinding in such a way that bone is capable of being punched out thereby in conjunction with the first tool element.

The stability of the sliding shaft can be increased in a simple manner if the sliding part material is a metal. In particular, the metal can be an instrument steel.

The manufacturing costs of the sliding shaft can be significantly reduced, if the sliding part material is a synthetic material. The manufacture of the sliding shaft in particular can be simplified in this way. For example, the sliding part can be produced from the synthetic material by means of an injection process. Due to the partial production of the second shaft part from a synthetic material, it is particularly suited to being a disposable item. If, for example, the second tool element is damaged or becomes unusable by virtue of a blunt cutting edge for example, then one merely needs to remove the second shaft part from the sliding shaft and replace it, whilst the first shaft part can continue to be used. This reduces the acquisition costs and especially too, reprocessing costs for the users of the sliding shaft.

Handling and also the safety of the sliding shaft can be improved in a simple manner if the tool part and the sliding part are connected inseparably to one another. The tool part and the sliding part then form the second shaft part which forms a single entity for the user, as is the case for conventional sliding shafts.

Advantageously, the tool part and the sliding part are connected together by welding, soldering or sticking. The connecting processes described are outstandingly suitable for inseparably connecting the tool part and the sliding part together and creating a unit forming the second shaft part.

It is advantageous, if the sliding part is produced by a process of moulding it onto the tool part. In particular in the case where the tool part is made of a metal, the sliding part can then be connected to the tool part in a second step by moulding it onto the latter. Hereby, the sliding part material could be a synthetic material in particular, but it could also be a metal.

In order to facilitate the process of connecting the tool part and the sliding part, it is expedient if the tool part has at least one connecting projection which protrudes in the proximal direction and is at least partially mouldable. The sliding part can then be moulded onto the tool part in a simple manner by over-moulding the connecting projection, whereby it is connected inseparably to the tool part.

The cleanability of the sliding shaft can be further improved in a simple manner if at least one rinsing through opening is formed in the sliding part.

It is advantageous, if the first tool element and the second tool element together form a punching tool and if the working position, in which the first and the second tool elements abut each other and cooperate, defines a punching position. This arrangement permits e.g. bones or cartilages to be removed in the desired manner by means of the sliding shaft instrument in the punching position thereof.

In accordance with the invention furthermore, the object posed hereinabove is achieved in the case of a surgical sliding shaft of the type described hereinabove in that the at least one first and/or second guide element is open in a direction facing away from the second shaft part and/or laterally.

The solution proposed in accordance with the invention makes it possible for the guidance device of the sliding shaft to be cleaned in a simple and reliable manner. Due for example to the provision of a lateral opening, the guidance device can be freed of impurities by means of a rinsing fluid in a simple and reliable manner.

Advantageously, the sliding shaft instrument comprises one of the sliding shafts described above. The sliding shaft instrument thus also exhibits the advantages mentioned in connection with the preferred embodiments of the sliding shafts described above.

An operating surgeon can handle the sliding shaft instrument in a simple and secure manner, if the instrument handle is in the form of a handle part which is arranged or formed at a proximal end of the sliding shaft.

In accordance with a preferred embodiment of the invention, provision may be made for the handle part to comprise a first and a second handle element which are arranged such as to be moveable relative to each other, and for the first handle element to be coupled to the first shaft part and for the second handle element to be coupled to the second shaft part. With such a construction, relative movement of the two handle parts can cause a relative movement of the two shaft parts with respect to each other in a simple manner.

The structure of the sliding shaft instrument can be further simplified in a simple manner, if the first and the second handle element are mounted on one another in moveable manner and define a clasping region. In particular, a clasping region is to be understood as being the region in which the handle elements are mounted on one another, in a manner similar to conventional shears for example.

It is advantageous furthermore, if the clasping region on the first shaft part and/or on the second shaft part and/or on the first and/or on the second handle element comprises at least one clasping region recess which, in any position of the first and second shaft parts relative to each other, is freely accessible through at least one clasping region opening which is of such a size as to prevent a capillary effect for a cleaning fluid. In contrast to known sliding shaft instruments, the clasping region opening also makes it possible for impurities in the clasping region to be removed by a rinsing process using a cleaning or a rinsing fluid for example. The cross-section of the clasping region opening can be of any shape, and it can, in particular, be in the form of a boring or have a polygonal cross section for example. Expediently, a minimum diameter or a minimum width of the clasping region opening lies in a range of from 0.2 mm up to 10 mm.

The structure of the sliding shaft instrument can be further simplified, if the first shaft part and the first handle element are connected immovably to one another. In particular, the two parts could also be formed in one piece manner, preferably from an instrument steel.

Actuating forces can be transferred from the second handle element to the second shaft part in a simple and reliable manner, if these are connected to one another in moveable manner.

A particularly simple structure of the sliding shaft instrument can be achieved, if the second handle element is coupled to the second shaft part in pivotal manner.

It can also be expedient, if the second handle element is mounted on the handle part in pivotal manner. Hence, in particular, mounting of the second handle element can be achieved independently of the first handle element.

Furthermore, in a further preferred embodiment of the invention, provision may be made for a restoring device for automatically moving the sliding shaft instrument back from a position in which it has been deflected from the rest position and the spacing between the first and the second tool element is smaller than it is in the rest position whereat the spacing between the first and the second tool element is a maximum. By virtue of a restoring device of this type, it can be ensured that the tool elements are spaced from each other when the sliding shaft instrument is unactuated. It can then be grasped by the user and is immediately ready for undertaking surgery therewith due to the cooperation of the tool elements in the desired manner.

The sliding shaft instrument can be constructed in a particularly simple and compact manner, if the restoring device is arranged on or is applied to the handle part. In the case of a forced coupling between at least one handle element of the handle part and at least one shaft part for example, the restoring device can then cause a relative movement of the shaft parts into the rest position due to the pressure on this handle element. The restoring device can be formed in a simple manner, if it comprises at least one restoring member. It is also conceivable for two or three restoring members to be provided. In particular, these can be arranged and/or formed in such a way that they engage one another directly and cooperate together.

It is expedient, if the restoring device comprises at least one biasing element which holds the sliding shaft instrument in the basic position.

The production of the sliding shaft instrument is further simplified, if the at least one biasing element or the at least one restoring member is in the form of a spring element. The spring element can be in the form of a coiled or a leaf spring in particular.

It is expedient, if the at least one biasing element is arranged on a projection of the first and/or second handle element. When using leaf springs in particular, the biasing element is thereby prevented in a simple manner from directly abutting the first or second handle element which has the disadvantage that fluid can again be sucked in between the handle element and the at least one biasing element due to a capillary effect. The spacing between the biasing element and the first and/or second handle element preferably amounts to at least 0.2 mm. Such a spacing can be achieved in a simple manner by means of a spacer element in the form of a projection or a washer for example.

In order to be able to punch out bone material from a bone in a simple and safe manner, it is expedient for the sliding shaft instrument to be in the form of a bone punch.

The invention further relates to a surgical sliding shaft instrument comprising an instrument handle and a sliding shaft that is operable by means of the instrument handle, which said sliding shaft defines a longitudinal direction and comprises a first shaft part and a second shaft part which are arranged such that they are displaceable relative to each other, which said first shaft part carries a first tool element and which said second shaft part carries a second tool element, wherein the second shaft part has a cut material collector having an inlet opening which is bounded by the second tool element and extends therefrom in the proximal direction, wherein the cut material collector has at least one emptying opening which is formed at the proximal side of the inlet opening, and the emptying opening is open in a lateral emptying direction, which said emptying direction is oriented perpendicularly or substantially perpendicularly to the longitudinal direction and parallel or substantially parallel to a contact plane defined by a lower surface of the second shaft part.

Moreover, the invention relates to a sliding shaft for a surgical sliding shaft instrument which defines a longitudinal direction and comprises a first shaft part and a second shaft part which are arranged such as to be displaceable relative to each other, wherein said first shaft part carries a first tool element and said second shaft part carries a second tool element, wherein the second shaft part comprises a cut material collector having an inlet opening which is bounded by the second tool part and extends therefrom in the proximal direction, wherein the second shaft part is formed in at least two parts, and comprises a tool part which comprises the second tool element and a sliding part which is connected to the tool part A first exemplary embodiment of a surgical sliding shaft instrument bearing the general reference symbol 10 is illustrated in FIG. 1 in the form of a bone punch 10 which is also referred to as an osteotome. It comprises a sliding shaft 12 consisting of a first shaft part 14 and a second shaft part 18 which is displaceable relative thereto in parallel with a longitudinal axis 16 defined by the sliding shaft 12.

The first shaft part 14 is of elongate parallelepipedal construction and, at the distal end thereof, it has a first tool element 20, namely, in the form of an anvil-like counter member 24 which protrudes from an upper surface 22 and forms a counter member for a cutting edge 26 that is arranged at a distal end of the second shaft part 18. In a rest position such as is illustrated in FIG. 1, the cutting edge 26 and the counter member 24 are spaced from each other. If the second shaft part 18 is moved relative to the first shaft part 14 in the distal direction, the cutting edge 26 which forms a second tool element 28 can press directly against the counter member 24 and thus work on bone or cartilage material in the desired manner. The tool elements 20 and 28 together form a punching tool 176.

A guidance device 30 for guiding a movement of the second shaft part 18 relative to the first shaft part 14 comprises a first guide element 32 in the form of an undercut guide groove 34 or a guide groove 34 of T-shaped cross section which is open in the direction of the second shaft part 18. The guide groove 34 extends over approximately one third of the overall length of the first shaft part 14. From a lower surface 36 of the second shaft part 18, there protrudes a second guide element 38 which is in the form of a guidance projection 40 and engages in shape-fitting manner in the guide groove 34 such that the two shaft parts 14 and 18 are only displaceable relative to each other in parallel with the longitudinal axis 16. At the proximal side thereof, the guide groove 34 adjoins an insertion slot 42 which serves to receive the guidance projection 40 when assembling the bone punch 10 until the lower surface 36 comes into contact with the upper surface 22 whereupon the guidance projection 40 can be brought into engagement with the guide groove 34 by moving the second shaft part 18 in the distal direction.

At a proximal end of the sliding shaft 12, there is arranged a handle part which bears the general reference symbol 44 and forms an instrument handle 45 that is connected inseparably to the sliding shaft and comprises a first handle element 46 and also a second handle element 48, said handle elements 46 and 48 also being referred to as so-called branches. The first handle element 46 is formed in one piece manner with the first shaft part 40 and projects laterally away therefrom at an angle of approximately 45° with respect to the longitudinal axis 16. The second handle element 48 is mounted on the first shaft part 14 in the region where it merges into the first handle element 46 such that it is pivotal about a pivotal axis 50 which runs in a direction that is perpendicular to the longitudinal axis 16. A coupling end 52 of the second handle element 48 extending beyond the pivotal axis 50 is pivotal about a pivotal axis 54 running parallel to the pivotal axis 50, is coupled to a proximal end 56 of the second shaft part 18 and defines an end region 58. The end 56 always projects beyond the upper surface 22 independently of a pivotal position of the handle elements 46 and 48 relative to each other. The pivotal axis 54 likewise always runs above the upper surface 22.

For the purposes of enabling the lower surface 36 to abut the upper surface 22 of the first shaft part 14 even in the vicinity of the proximal end 56, the second shaft part 18 is provided with an end region recess 60 which is open in the direction of the first shaft part 14 and into which the end 56 extends. The pivotal axis 54 runs within the region or section of the second shaft part 18 defined by the end region recess 60.

Furthermore, the bone punch 10 comprises a restoring device 62 having two restoring members 64 and 66 in the form of leaf springs. First free ends of the restoring members 64 and 66 are fixed to the respective free ends 72 and 74 of the first and second handle elements 46, 48 by means of a respective screw 68 and 70, namely, to the inner surfaces 76 and 78 thereof. The free ends of the restoring members 64 and 66 that are not fixed to the handle elements 46, 48 are connected to one another in pivotal manner by means of a ball joint 80, namely, in such a way that the restoring device 62 holds the ends 72 and 74 away from each other in a basic position. The second handle element 48 can then be pivoted towards the first handle element 46 against the effect of the restoring device 62, whereby, due to the articulated connection between the second handle element 48 and the second shaft part 18, the latter can be simultaneously moved in the distal direction. If a user lets go of the handle part 44 of the bone punch 10, the restoring device 62 forces the bone punch 10 back into the basic position thereof which is illustrated in FIG. 1.

In order to improve the cleanability of the bone punch 10, various alterations have been made thereto compared with the bone punches known from the state of the art.

Firstly, the bone punch 10 comprises a cleaning gap 82 which is formed by an even slot 84 on the lower surface 36 of the second shaft part 18, namely, over the entire width of the shaft part 18 transverse to the longitudinal axis 16. The slot 84 has a depth falling within a range of between 0.3 mm and 0.9 mm so that a spacing defined by the cleaning gap 82 between the first shaft part 14 and the second shaft part 18 corresponds to the depth of the slot 84 in the region of the cleaning gap 82. The cleaning gap 82 extends in the direction of the longitudinal axis 16 starting approximately from the end region recess 60 to an area close to the guidance projection 40. A guidance region 86 of the bone punch 10 is then defined by a section of the second shaft part 18 adjoining the slot 84 on the distal side in conjunction with the guide groove 34. The width of the cleaning gap 82 i.e. the depth of the slot 84 is selected in such a way as to prevent a capillary effect for a cleaning fluid. The slot 84 located opposite the upper surface 22 is thus freely accessible for cleaning purposes by means of a cleaning or a rinsing fluid.

Next, the guide groove 34 is opened up laterally facing away from the second shaft part 18, namely, by means of two rinsing openings 88 and 90 which are separated from each other by a transverse web 92. The rinsing openings 88 and 90 which are constructed in the form of slots or elongate holes form a fluid connection between a lower surface 94 of the first shaft part 14 and a guidance space 96 defined by the guide groove 34. Consequently, the guide groove 34 can also be optimally cleaned by means of a cleaning and rinsing fluid. In addition, the rinsing opening 90 provided at the proximal side of the web is in fluid connection with the insertion slot 42 which is located at least partially opposite the slot 84, namely, independently of the position of the shaft parts 14 and 18 relative to each other.

In order to improve the cleanability of the bone punch 10 in the end region 58 even more, there is provided an end region opening 98 in the form of a through opening which opens up the end region recess 60, and, for example, is in the form of a boring or a slot which produces a fluid connection between the end region recess 60 and an upper surface 100 of the second shaft part 18. The end region recess 60 can thus be optimally cleaned since it is in fluid connection with the slot 84 on the one hand and with the upper surface 100 on the other.

The cleanability of the bone punch 10 was also improved in the region of the handle part 44 compared with known sliding shaft instruments. Between the ends of the restoring members 64 and 66 that are fixed in place by the screws 68 and 70 and the handle elements 46 and 48, there is a respective spacer element which, for example, is in the form of a washer 102 or 104 and keeps the restoring members 62 and 64 spaced from the handle elements 46 and 48, at least in the basic position illustrated in FIG. 1.

In this way, respective gaps 106 and 108 are formed between the restoring members 64 and 66 and the handle elements 46 and 48, the widths of the gaps, i.e. the spacing between the restoring members 64 and 66 on the one hand and the handle elements 46 and 48 on the other, corresponding approximately to the thickness of the washers 102 and 104. The thickness of the washers 102 and 104 preferably lies in a range between 0.4 mm and 1 mm.

All the parts of the bone punch 10 are preferably made of a rustproof instrument steel.

A further exemplary embodiment of a bone punch bearing the general reference symbol 10' which is illustrated in FIGS. 4 to 7 comprises a sliding shaft 12' and an instrument handle 45' that is connectable thereto in releasable manner. The instrument handle 45' and the sliding shaft 12' are connectable to one another in releasable manner by means of a coupling device 110.

The basic construction of the sliding shaft 12' corresponds to that of the sliding shaft 12 and it comprises a first shaft part 14' and also a second shaft part 18' which are coupled to one another by means of a guidance device 30'.

Coupling projections which protrude from a lower surface 94' of the first shaft part 14' and define coupling elements 112 and 114 are formed at a proximal end of the first shaft part 14' or somewhat spaced therefrom, said projections being adapted to be brought into engagement with corresponding coupling elements 116 and 117 provided on the instrument handle 45' in order to arrange the first shaft part 14 thereon such as to be immovable relative to the instrument handle 45'.

The instrument handle 45' comprises a drive 118 in the form of a pneumatic cylinder which is coupled to an angled and pivotally mounted drive member 120 which, in turn, is adapted to be brought into engagement with a drive member seating 122 that is formed in a proximal end region of the second shaft part 18'. The drive 118 can thus be used for moving the second shaft part 18' relative to the first shaft part 14' in the distal direction in parallel with the longitudinal axis 16. An example of a pneumatically driven or operable instrument handle is described in DE 20 2004 015 643 U1 which, together with the entire contents thereof, is incorporated into this description.

The first shaft part 14' is constructed in the form of an elongate, substantially parallelepipedal body 124 and has a first tool element 20' located at the distal end thereof, namely, in the form of an anvil-like counter member 24' for a cutting edge 26' disposed at a distal end of the second shaft part 18' which projects from an upper surface 22'. In a rest position such as is illustrated in FIG. 4, the cutting edge 26' and the counter member 24' are spaced from each other. If the second shaft part 18' is moved relative to the first shaft part 14' in the distal direction, the cutting edge 26', which forms a second tool element 28', can press directly on the counter member 24 and thereby work upon bones and cartilage material in the desired manner. It should be mentioned that the cutting edge 26' defines a cutting plane 126 which is inclined to a certain extent with respect to the longitudinal axis 16.

A guidance device 30' for guiding the movement of the second shaft part 18' relative to the first shaft part 14' comprises a first guide element 32' in the form of an undercut guide groove 34' or a guide groove 34' having a T-shaped cross section which is open in the direction of the second shaft part 18'. The guide groove 34' extends over approximately one fifth of the overall length of the first shaft part 14'. A second guide element 38' in the form of a guidance projection 40' protrudes from a lower surface 36' of a tool part 128 forming a distal end section of the first shaft part 18', said second guide element engaging in the guide groove 34' in substantially interlocking manner in such a way that the two shaft parts 14' and 18' are only displaceable relative to each other in parallel with the longitudinal axis 16.

At the proximal side of the guide groove 34', the latter is adjoined by an insertion slot 42' which serves to receive the guidance projection 40' when assembling the sliding shaft 12' until the lower surface 36' can be brought into contact with the upper surface 22' of the first shaft part 18' whereupon the guidance projection 40' can be caused to engage in the guide groove 34' by moving the shaft part 18' in the distal direction.

The second shaft part 18' is formed in two-piece manner and comprises the tool part 128 and also a sliding part 130 which adjoins the latter at the proximal side and in which the drive member seating 122 is formed. The tool part 128 is in the form of a sleeve and, at the distal end thereof, it comprises the cutting edge 26' which is formed by grinding an outer surface 132 of the tool part 128 in the vicinity of its distal end. The cutting edge 26' bounds an inlet opening 134 into the interior 136 of the tool part 128 which extends in the proximal direction and forms a collecting means 138 for the cut material.

The internal cross-sectional area 140 of the cut material collector 138 increases continuously from the inlet opening 134 in the proximal direction, i.e. it becomes larger. The smallest cross-sectional area thus defines the inlet opening 134. The largest cross-sectional area 140 of the cut material collector 138 is at the proximal end 142 thereof. Commencing therefrom in the distal direction, there are emptying openings 150 which extend in a wall 144 of the second shaft part 18' and are symmetrical with respect to a centre plane 146 that simultaneously defines a plane of symmetry of the sliding shaft 12', said emptying openings opening out in an emptying direction 148 which extends in parallel with a perpendicular to the centre plane 146. The height of the emptying openings 150 in a direction that is both perpendicular to the emptying direction 148 and also to the longitudinal axis 16 corresponds to the height of the cut material collector 138. The emptying openings 150 are about three times as long as they are broad, the distal and proximal ends 152 and 154 thereof being rounded.

Adjoining the proximal end 142 on the proximal side, there is a connecting projection 156 on which the sliding part 130 is formed by a moulding process. The tool part 128 is preferably made of an instrument steel, the sliding part 130 of an injection mouldable synthetic material. The sliding part 130 is thus made of a sliding part material and the tool part 128 of a tool part material which are selected differently in the present case, namely, a synthetic material on the one hand and a metal on the other. Alternatively, the sliding part 130 could also be moulded separately and subsequently be connected to the tool part 128 by adhesion or welding in the region of the connecting projection 156. Self evidently, the sliding part 130 could also be made of a metal so that it can be connected to the tool part 128 by adhesion, soldering or welding.

Elongate slit-like rinsing through openings 158 are formed in the sliding part 130 on the proximal side of the connecting projection 156, in the case of the exemplary embodiment of the sliding shaft 12' illustrated in FIG. 5, there is a total of three rinsing through openings 158 which extend from the upper surface 100' of the second shaft part 18' up to the lower surface 36' thereof.

For the purposes of improved guidance of the movement of the second shaft part 18' relative to the first shaft part 14', projections that project in the direction of the second shaft part 18' and which are of T-shaped cross section perpendicularly to the longitudinal axis 16 can be formed on the first shaft part 14', said projections extending in parallel with the longitudinal axis 16 over approximately one third of the length of the rinsing through openings.

Optionally, for the purposes of constructing guidance devices that are not illustrated in FIGS. 4 and 5, projecting, mutually facing web-like guidance projections can be arranged or formed on internal side walls that extend in parallel with the longitudinal axis 16, said guidance projections defining therebetween a guidance slot extending in parallel with the longitudinal axis 16 for a respective one of the T-shaped projections. In other words, the guidance projections define T-shaped guide grooves for the T-shaped projections. The guidance projections extend over somewhat less than two thirds of the length of the rinsing through opening 158 in parallel with the longitudinal axis, namely, commencing from the proximal end of the respective rinsing through opening 158. In this way, the T-shaped projections can be introduced simultaneously from below in the vicinity of the distal ends of the rinsing through openings 158 and inserted into the guidance slot defined between the guidance projections by a movement of the second shaft part 18' relative to the first shaft part 14' in the distal direction. In this way, the first shaft part 14' and the second shaft part 18' are held together in guided manner even in the region of the sliding part.

Due to the special arrangement and design of the rinsing through openings 158, the guidance devices optionally provided in the vicinity thereof by the T-shaped projections on the first shaft part 14' and the guidance projections provided on the internal side walls of the rinsing through openings 158 can be formed such as to be continuously open thereby facilitating cleaning of the bone punch 10.

As already described, the second shaft part 18', which comprises the sliding part 130 and also the tool part 128, can be manufactured, in particular, by moulding the sliding part 130 onto the tool part 128. Conceivable moulding processes are, for example, synthetic material injection moulding, metal injection moulding ("metal injection molding" or other so-called "MIM" techniques) or by ceramic injection moulding followed by a sintering process ("ceramic injection molding" or other so-called "CIM" techniques). An injection mould is needed here in each case. The provision of rinsing through openings 158 particularly in the region of the guidance devices optionally provided by the T-shaped projections on the first shaft part 14' and the guidance projections provided on the internal side walls of the rinsing through openings 158 has then the advantage that the injection mould for the sliding part can then be constructed in a relatively simple manner, namely in particular, without tool pushers.

Optionally, the cut material collector 138 could be open in the direction of the first shaft part 14' and closed thereby. In the present case furthermore, the projection area of a projection of the inlet opening cross-sectional area onto a plane perpendicular to the longitudinal direction 16 is smaller than any cross-sectional area 140 of any cross section of the cut material collector 138 parallel to the projection area. As already stated, the internal cross-sectional area 140 of the cut material collector 138 increases from the inlet opening 134 in the proximal direction, even being monotonic in the exemplary embodiment illustrated in the Figures. In the present case, the cut material collector 138 extends in conical manner from the inlet opening 134 in the proximal direction. Consequently, the emptying openings 150 are formed in a region of the cut material collector 138 that has the largest internal cross-sectional area 140.

In addition, the emptying openings 150 face sideways, in other words, they are open in the lateral direction. They permit the cut material collector 138 to be emptied in a simple manner when it has been filled with cut material in the form of a plurality of successively accomplished punching processes. In particular, the distal end of the sliding shaft 12' can remain in an operational area, if for example, an assistant of the operating surgeon occasionally empties the cut material collector 138 by inserting an auxiliary instrument such as a small pin for example into one emptying opening 150 and pushing the cut material that has collected in the cut material collector 138 laterally out of the cut material collector 138 through the other emptying opening 150. The bone punch 10' is thereby prepared in a rapid and simple manner for further punching processes which the operating surgeon can implement.

The actual part of the sliding shaft 12' subject to wear, namely, the cutting edge 26' is located on the sliding shaft 12'. This cutting edge can become blunt due to punching out hard bone material so that the entire sliding shaft 12' becomes practically useless. In principle, it is possible to resharpen the cutting edge 26' by regrinding the outer sides 132 for example.

However, due to the two-piece construction of the second shaft part 18', this could also be made in the form of a disposable item so that the first shaft part 14' which is not subjected to wear from a practical point of view can continue to be used whereas the second shaft part 18' can be replaced by a new second shaft part 18' that still has a sharp cutting edge 26'. The two-piece construction of the second shaft part 18' thus permits just the tool part to be made of a material suitable for forming a cutting edge 26' whereas the remaining part of the second shaft part 18' can be made of a more economical and easily machinable material such as a synthetic material for example.

In order to enable the first shaft parts 14' and the second shaft parts 18' to be combined with one another in practically any manner, it is necessary to provide for or permit adequate manufacturing tolerances in the region of the guidance device 30' in order to be able to selectively place the first and second guide elements 32' and 38' in contact with one another. Nevertheless, in order to ensure that tissue and bone can be worked on by the sliding shaft 12' in the customary precise manner, there is provided a tolerance compensating device 160 for compensating for the manufacturing tolerances of the cooperating guide elements 32' and 38'. In particular, they are arranged and formed in such a manner that manufacturing tolerances are compensated for in the working position in which the first and second tool elements 20' and 28' cooperate for working on tissue or bone, i.e. especially when they fit together as illustrated in FIG. 6.

The tolerance compensating device 160 comprises a pressure device 162 for biasing the second guide element 38' against the first guide element 32'. In the exemplary embodiment illustrated in the Figures, it is arranged or formed on the second guide element 38', however it could also be arranged or formed on the first guide element 32'. The pressure device 162 comprises a biasing element 164 for biasing the second guide element 38' against the first guide element 32'. In turn, the biasing element 164 is in the form of a spring element 166, namely, in the form of a leaf spring which extends between two projections 168 that protrude from the lower surface 36' of the tool part 128 and each of which forms a respective part of the guidance device 30' and the guidance projection 40'. The spring element 160 is curved away from the lower surface 36' in a slightly convex manner and abuts a base 170 of the guide groove 34' facing in the direction of the second shaft part 18. The guidance projection 40' is thus pressed against internal boundary surfaces 172 of the guide groove 34' that face in the direction of the base 170 and thereby compensates for manufacturing tolerances in the region of the guide groove 34' or the guidance projection 40'. In the working position, the lower surface 36' can be spaced somewhat from the first shaft part 14' in the region of the tool part 128 due to the special construction of the tolerance compensating device 160.

The counter member 24' which is also referred to as an anvil member is of such a size as to prevent the cutting edge 26' of the second shaft part 18' being pushed over an upper edge 174 of the counter member 24' in order to ensure the cutting effect of the tool elements 20' and 28' that form a punching tool 176 in every case. Compensation for the tolerances of the guidance device 30' which is at least partially resilient due to the spring element 166 is thus at most as great as the distance of the cutting edge 26' from the upper edge 174.

In order in particular to be able to easily clean the first re-usable shaft part 14', there is provided at the proximal side of the guide groove 34' a rinsing opening 88' which is analogous to the rinsing opening 88 in the bone punch 10. In particular, there is a fluid connection between said rinsing opening 88' and the guide groove 34'.

The biasing element 164 and the second guide element 38' are formed in one piece manner in the exemplary embodiment illustrated in the Figures. Furthermore, the biasing element 164 is moveable against the force exertable thereby from a basic position, in which the spacing between a pressure surface 178 facing away from the second shaft part 18' and the lower surface 36' of the second shaft part 18' is at its maximum into a pressure position such as is illustrated in FIG. 6 for example in which the spacing between the pressure surface 178 facing away from the second shaft part 18' and the lower surface 36' of the second shaft part 18' is a minimum.

The biasing element 164 and the tolerance compensating device 160 as a whole are mirror-symmetrical with respect to a mirror plane 180 extending perpendicularly relative to the longitudinal axis 16. Equally, the proximal and distal ends of the biasing element 164 are held on the second guide element 38'.

An alternative exemplary embodiment of a sliding shaft of a bone punch 10" is partially illustrated in FIG. 8 and bears the general reference symbol 12" therein. The sliding shaft 12" differs from the sliding shaft 12' only in respect of the construction of the guidance device 30" and the tolerance compensating device 160 so that the same reference symbols are used for mutually corresponding parts or identical reference numbers are provided with two apostrophes ("'"') for identification purposes.

A biasing element 164' in the form of a spring element 166' which is formed in the manner of a leaf spring protrudes from the guidance projection 40" in the proximal direction and somewhat in the direction of the first shaft part 14". Said biasing element is supported on the base 170' of the guide groove 34" by a pressure surface 178'. The pressure device 162' of the tolerance compensating device 160' first displays its effect only when the proximal end 182 of the biasing element 164 comes into engagement with the guide groove 34" i.e. just shortly before reaching the working position illustrated in FIG. 8 as well as in the working position and then presses the lower surface 36" somewhat away from the upper surface 22".

In analogous manner to the sliding shaft 12', the sliding shaft 12" is connectable to the instrument handle 45' in releasable manner.

The invention claimed is:

1. A sliding shaft for a surgical sliding shaft instrument which defines a longitudinal direction and comprises:
    a first shaft part and a second shaft part which are arranged such as to be displaceable relative to each other,
    said first shaft part carrying a first tool element and said second shaft part carrying a second tool element,
    the second shaft part comprising a cut material collector having an inlet opening which is completely bounded by a cutting edge of the second tool element, the cut material collector extending from the inlet opening in a proximal direction,
    the cut material collector comprising at least one emptying opening which is formed on a proximal side of the inlet opening, the at least one emptying opening being open in a lateral emptying direction, which emptying direction is oriented perpendicularly or substantially perpendicularly to the longitudinal direction and parallel or substantially parallel to a contact plane defined by a lower surface of the second shaft part,
    wherein an internal cross sectional area of the cut material collector continuously increases from a distal end of the cutting edge of the second tool element in the proximal direction.

2. The sliding shaft in accordance with claim 1, wherein the cut material collector is open in a direction of the first shaft part and the first shaft part closes the cut material collector completely.

3. The sliding shaft in accordance with claim 2, wherein the first shaft part completely closes an opening of the cut material collector facing in the direction of the first shaft part.

4. The sliding shaft in accordance with claim 1, wherein an inlet opening cross-sectional area of the inlet opening is smaller than a cross-sectional area of any cross section of the cut material collector parallel to the inlet opening cross-sectional area.

5. The sliding shaft in accordance with claim 1, wherein the at least one emptying opening is formed in a region of the cut material collector that has a largest or substantially the largest internal cross-sectional area.

6. The sliding shaft in accordance with claim 1, wherein the at least one emptying opening extends up to a proximal end or substantially up to the proximal end of the cut material collector.

7. The sliding shaft in accordance with claim 1, wherein a length of the at least one emptying opening parallel to the longitudinal direction is at least twice as large as a width of the emptying opening in a direction perpendicular to the longitudinal direction and to the emptying direction.

8. The sliding shaft in accordance with claim 1, wherein boundaries of the at least one emptying opening in at least one of a distal direction and the proximal direction are rounded.

9. The sliding shaft in accordance with claim 1, wherein the second shaft part is formed in at least two parts, and comprises a tool part which comprises the second tool element and a sliding part which is connected to the tool part.

10. The sliding shaft in accordance with claim 9, wherein the tool part comprises the cut material collector.

11. The sliding shaft in accordance with claim 9, wherein the sliding part is made of a sliding part material and the tool part is made of a tool part material.

12. The sliding shaft in accordance with claim 11, wherein the tool part material and the sliding part material are different materials.

13. The sliding shaft in accordance with claim 11, wherein at least one of the tool part material and the sliding part material is a metal, in particular an instrument steel.

14. The sliding shaft in accordance with claim 11, wherein the sliding part material is a synthetic material.

15. The sliding shaft in accordance with claim 9, wherein the tool part and the sliding part are connected inseparably to one another.

16. The sliding shaft in accordance with claim 15, wherein the tool part and the sliding part are connected together by welding, soldering or adhesion.

17. The sliding shaft in accordance with claim 15, wherein the sliding part is molded onto the tool part.

18. The sliding shaft in accordance with claim 9, wherein the tool part has at least one connecting projection which protrudes in the proximal direction and is at least partially moldable.

19. The sliding shaft in accordance with claim 9, wherein the tool part is open at the proximal side and the sliding part closes the tool part at the proximal side.

20. The sliding shaft in accordance with claim 1, wherein:
the first tool element and the second tool element together form a punching tool, and
a working position, in which the first and the second tool elements abut each other and cooperate, defines a punching position.

21. The sliding shaft in accordance with claim 1, wherein the emptying opening is open during use of the instrument.

22. A surgical sliding shaft instrument comprising:
an instrument handle, and
a sliding shaft that is operable by means of the instrument handle, said sliding shaft defining a longitudinal direction and comprising a first shaft part and a second shaft part which are arranged such that they are displaceable relative to each other, said first shaft part carrying a first tool element and said second shaft part carrying a second tool element, the second shaft part comprising a cut material collector having an inlet opening which is completely bounded by a cutting edge of the second tool element, the cut material collector extending from the inlet opening in a proximal direction, the cut material collector comprising at least one emptying opening which is formed at a proximal side of the inlet opening, and the emptying opening being open in a lateral emptying direction, said emptying direction being oriented perpendicularly or substantially perpendicularly to the longitudinal direction and parallel or substantially parallel to a contact plane defined by a lower surface of the second shaft part,
wherein an internal cross sectional area of the cut material collector continuously increases from a distal end of the cutting edge of the second tool element in the proximal direction.

23. The sliding shaft instrument in accordance with claim 22, wherein the cut material collector is open in a direction of the first shaft part and the first shaft part closes the cut material collector completely.

24. The sliding shaft instrument in accordance with claim 22, wherein the instrument handle and the sliding shaft are connectable to one another in a releasable manner.

25. A sliding shaft for a surgical sliding shaft instrument which defines a longitudinal direction and comprises:
a first shaft part and a second shaft part which are arranged such as to be displaceable relative to each other, said first shaft part carrying a first tool element and said second shaft part carrying a second tool element,
the second shaft part comprising a cut material collector having an inlet opening which is completely bounded by a cutting edge of the second tool element, the cut material collector extending from the inlet opening in a proximal direction,
the second shaft part being formed in at least two parts, comprising a tool part which comprises the second tool element and a sliding part which is connected to the tool part,
wherein an internal cross sectional area of the cut material collector continuously increases from a distal end of the cutting edge of the second tool element in the proximal direction.

\* \* \* \* \*